US012557860B2

(12) United States Patent
Lee et al.

(10) Patent No.: US 12,557,860 B2
(45) Date of Patent: Feb. 24, 2026

(54) PHOTOCATALYTIC FACIAL MASK AND METHOD FOR MANUFACTURING THE SAME

(71) Applicant: CENTER FOR ADVANCED META-MATERIALS, Daejeon (KR)

(72) Inventors: Sueng-Mo Lee, Nonsan-si (KR); Bongkyun Jang, Daejeon (KR); Jae-Hyun Kim, Daejeon (KR)

(73) Assignee: CENTER FOR ADVANCED META-MATERIALS, Daejeon (KR)

( * ) Notice: Subject to any disclaimer, the term of this patent is extended or adjusted under 35 U.S.C. 154(b) by 993 days.

(21) Appl. No.: 17/697,329

(22) Filed: Mar. 17, 2022

(65) Prior Publication Data

US 2022/0296766 A1     Sep. 22, 2022

(30) Foreign Application Priority Data

Mar. 18, 2021     (KR) ........................ 10-2021-0035444

(51) Int. Cl.
| | |
|---|---|
| *A41D 13/11* | (2006.01) |
| *A61L 9/20* | (2006.01) |
| *A62B 23/02* | (2006.01) |

(52) U.S. Cl.
CPC .............. *A41D 13/11* (2013.01); *A61L 9/205* (2013.01); *A62B 23/02* (2013.01); *A61L 2209/12* (2013.01); *A61L 2209/14* (2013.01)

(58) Field of Classification Search
CPC .......... A61H 7/10; A61H 18/00; A61H 18/02; A61H 18/025; A61H 23/00; A61H 23/02; A61H 23/025; A61H 23/06; A41D 13/11; A41D 13/1107; A41D 13/1115; A41D 13/1123; A41D 13/113; A41D 13/1138; A41D 13/1146; A41D 13/1153; A41D 13/1161; A41D 13/1169; A41D 13/1176; A41D 13/1184; A41D 13/1192
See application file for complete search history.

(56) References Cited

U.S. PATENT DOCUMENTS

| | | | |
|---|---|---|---|
| 2005/0249660 A1* | 11/2005 | Liao ......................... | C01G 9/03 |
| | | | 423/622 |
| 2008/0083411 A1* | 4/2008 | Guth ...................... | A62B 18/08 |
| | | | 95/285 |
| 2015/0216241 A1* | 8/2015 | Lee .................... | A41D 13/1192 |
| | | | 128/863 |
| 2020/0069730 A1* | 3/2020 | Okazaki ............... | A61K 33/242 |

(Continued)

FOREIGN PATENT DOCUMENTS

| | | | |
|---|---|---|---|
| CN | 205082705 U | * | 3/2016 |
| JP | 2018528072 A | * | 9/2018 |

(Continued)

*Primary Examiner* — Colin W Stuart
(74) *Attorney, Agent, or Firm* — Hauptman Ham, LLP

(57)     ABSTRACT

In a photocatalytic facial mask and a method for manufacturing the photocatalytic facial mask, the facial mask includes an inner layer, an outer layer, and a functional filter layer. The functional filter layer is disposed between the inner layer and the outer layer. The functional filter layer includes a photoactive layer, the photoactive layer includes a photocatalytic fiber having a core-shell structure, and the core-shell structure includes a core having a polymer fiber and a shell having a photocatalyst disposed at the core.

14 Claims, 11 Drawing Sheets

(56) References Cited

U.S. PATENT DOCUMENTS

2021/0052488 A1* 2/2021 Okazaki ................ A61M 15/00
2022/0007756 A1* 1/2022 Chan .................. A41D 13/1107
2022/0118125 A1* 4/2022 Dawkins ............... A41D 13/11
2022/0118295 A1* 4/2022 Busby ............... B01D 39/1692

FOREIGN PATENT DOCUMENTS

KR      10-2017-0096359 A      8/2017
WO      WO-2010079626 A1 *   7/2010    ......... A41D 13/1138

* cited by examiner

CA = 134 ± 2°

CA = 126 ± 2°

CA = 0°

CA = 0°

PHOTOCATALYTIC FACIAL MASK AND METHOD FOR MANUFACTURING THE SAME

CROSS-REFERENCE TO RELATED APPLICATION

This application claims priority under 35 U.S.C. § 119 to Korean Patent Application No. 10-2021-0035444, filed on Mar. 18, 2021, the disclosure of which is incorporated by reference herein in its entirety.

BACKGROUND

1. Field of Disclosure

The present disclosure of invention relates to a photocatalytic facial mask and a method for manufacturing the photocatalytic facial mask, and more specifically the present disclosure of invention relates to a photocatalytic facial mask capable of operating all the time and a method for manufacturing the photocatalytic facial mask.

2. Description of Related Technology

Conventionally, a facial mask is used for cold protection or to perform a dustproof or gas-proof function in an industrial field. However, recently, the facial mask is mainly used for the prevention of respiratory diseases caused by fine dust in daily life, for public quarantine in society, for prevention of infection and contamination by bacteria or scattering secretions, and so on.

Since the conventional mask having merely cotton material is less effective in blocking microscopic harmful gases, bacteria, and so on, to prevent the above infection and contamination, the technology in which a photocatalytic layer is formed on an outer skin to decompose harmful gases has been developed.

A photocatalyst generates an electron $e^-$ and a hole $h^+$ by irradiation of light, and the electron $e^-$ is reacted with oxygen existing on a surface of the photocatalyst to generate a superoxide anion $O^{2-}$, the hole $h^+$ forms hydroxide OH radical having a strong oxidizing effect, and thus the photocatalyst has a stronger oxidizing power than chlorine or ozone. According to the above reaction, the photocatalyst has effects such as UV protection, contamination protection, air purification, sterilization, odor removal, and so on.

However, the facial mask using the photocatalyst has difficulties to be multi-used, since the technology in which the photocatalyst is coated on a coated layer such as a non-woven fabric and then is attached to an outer surface of the facial mask is applied so that the coated layer of the photocatalyst may be detached in a cleaning. In addition, by-products generated through photocatalytic decomposition may be penetrated into the respiratory system through the facial mask. Further, when the light for activation of the photocatalyst does not exist or less exist, or when the light is hard to reach the photocatalyst, the effects of the photocatalyst mentioned above are hard to expect.

Thus, the photocatalytic facial mask is capable of being multi-used, preventing the detach or the decomposition of the photocatalyst in the cleaning, and operating all the time without being run out of or decreasing photocatalytic activity due to an external environment.

Related prior art is Korean Laid-open Patent No. 10-2017-0096359.

SUMMARY

The present invention is developed to solve the above-mentioned problems of the related arts. The present invention provides a photocatalytic facial mask having a functional filter layer capable of operating the activity of a photocatalytic layer all the time regardless of the existence of the light in an external environment. Here, in the photocatalytic facial mask, a photoactive layer is operated all the time in the external environment with or without the light, and thus the facial mask has the photocatalytic activity regardless of the existence of the light. Further, the photocatalytic facial mask is capable of being cleaned and multi-used, since the functional filter layer is disposed between an inner layer and an outer layer of the mask to be detached easily.

In addition, the present invention also provides a method for manufacturing the photocatalytic facial mask.

According to an example embodiment, the facial mask includes an inner layer, an outer layer, and a functional filter layer. The functional filter layer is disposed between the inner layer and the outer layer. The functional filter layer includes a photoactive layer, the photoactive layer includes a photocatalytic fiber having a core-shell structure, and the core-shell structure includes a core having a polymer fiber and a shell having a photocatalyst disposed at the core.

In an example, the functional filter layer may further include a light irradiation layer having a light source configured to irradiate light to the photoactive layer. The light irradiation layer and the photoactive layer may be laminated with each other.

In an example, the shell of the photocatalytic fiber may have a plurality of sheath layers in which at least two kinds of photocatalyst are laminated at the core.

In an example, the photocatalytic fiber may include a first sheath layer having zinc oxide (ZnO) at the core, and a second sheath layer having titanium dioxide ($TiO_2$) on the first sheath.

In an example, the shell of the photocatalytic fiber may have a thickness between about 1 nm and about 100 nm.

In an example, a ratio of the thickness between the first sheath layer and the second sheath layer may be between about 8:1 and about 2:2.

In an example, a water contact angle of the photoactive layer may be less than about 45°.

In an example, the light irradiation layer may include an electrode, the light source, and a battery disposed on a surface of a textile.

In an example, the light source may irradiate ultraviolet rays having a wavelength between about 200 nm and about 400 nm.

In an example, the functional filter layer may have a kirigami pattern.

According to another example embodiment, in a method for manufacturing a facial mask, the photocatalyst is coated on a surface of polymer fibers, to form a photoactive layer including a photocatalytic fiber having a core-shell structure. An electrode is formed on a surface of a textile and a light source is attached, to form a light irradiation layer. The photoactive layer and the light irradiation layer are combined with each other, to form a functional filter layer. The functional filter layer is inserted between an inner layer and an outer layer of the facial mask.

In an example, the photocatalyst may be coated via an atomic layer deposition (ALD) or a chemical vapor deposition (CVD).

In an example, the photocatalytic fiber may be formed by coating the first photocatalyst on the surface of the polymer fiber and coating the second photocatalyst on the first photocatalyst.

According to the present example embodiments, in the facial mask, the photoactive layer having a core-shell structure photocatalytic fiber is disposed between the inner layer and outer layer, and thus the photocatalytic activity may be generated in the irradiation of the light, and excellent antibacterial properties may be performed. In addition, the functional filter layer having a laminated structure of the light irradiation layer is used, so that the photocatalytic activity may operate all the time regardless of the irradiation of the light, the time, and the location. Here, the light irradiation layer has the light source irradiating the light to the photoactive layer.

In addition, the functional filter layer is disposed between the inner layer and the outer layer of the mask, and thus the functional filter layer is protected from the contamination or the damage from outside, and the user easily inserts the functional filter layer between the inner layer and the outer layer or detaches the functional filter layer.

Further, the photoactive layer included in the photocatalytic facial mask has the core-shell structure in which the core has a polymer fiber and the shell having the photocatalyst disposed at the core. Thus, selective charge separation at the core-shell interface and suppression of the recombination of the electrons and the electron holes are performed so that the photocatalytic activity may be efficiently obtained.

Figure 1A:
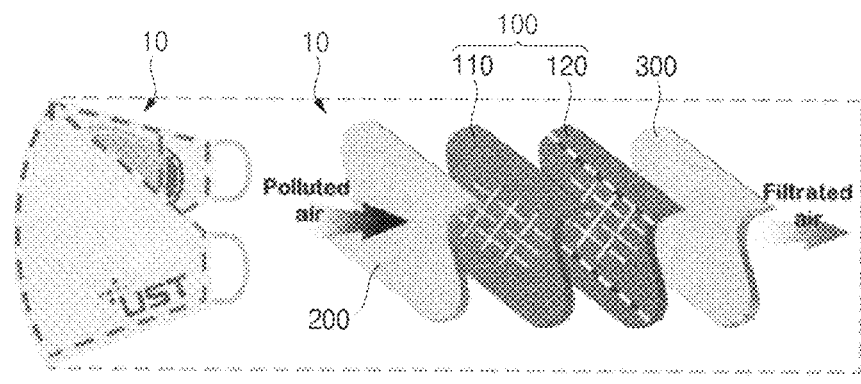
FIG. 1A is an exploded perspective view illustrating a photocatalytic facial mask according to an example embodiment of the present invention.

| * Reference numerals | |
| --- | --- |
| 10: photocatalytic facial mask | 100: functional filter layer |
| 110: photoactive layer | 111: photocatalytic fiber |
| 120: light irradiation layer | 200: outer layer |
| 300: inner layer | 400: core |
| 410: first sheath layer | 420: second sheath layer |

DETAILED DESCRIPTION

The invention is described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. In the drawings, the size and relative sizes of layers and regions may be exaggerated for clarity.

It will be understood that, although the terms first, second, third, etc. may be used herein to describe various elements, components, regions, layers, and/or sections, these elements, components, regions, layers, and/or sections should not be limited by these terms. These terms are only used to distinguish one element, component, region, layer, or section from another region, layer, or section. Thus, a first element, component, region, layer, or section discussed below could be termed a second element, component, region, layer, or section without departing from the teachings of the present invention.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" can encompass both an orientation of above and below. The device may be otherwise oriented (rotated 90 degrees or at other orientations) and the spatially relative descriptors used herein interpreted accordingly.

The terminology used herein is to describe particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The photocatalytic facial mask (hereinafter, the facial mask) according to the present exemplary embodiments of the present invention may solve the temporal and spatial constraints of photocatalytic activity of the conventional mask having the photocatalyst, may have excellent photocatalytic activity, may be easy to be cleaned and may be used with plural times.

Here, in the facial mask according to the present example embodiments, a functional filter layer is disposed between an inner layer and an outer layer of the facial mask, and the functional filter layer includes a photoactive layer which includes a photocatalytic fiber having a core-shell structure.

Hereinafter, the invention is described more fully hereinafter with reference to the accompanying drawings, in which embodiments of the invention are shown.

FIG. A is an exploded perspective view illustrating a photocatalytic facial mask according to an example embodiment of the present invention. FIG. 1B is a conceptual view illustrating a photoactive layer and a light irradiation layer of the photocatalytic facial mask of FIG. 1A.

The facial mask 10 according to the present exemplary embodiment includes an inner layer 300, an outer layer 200, and a functional filter layer 100. The functional filter layer 100 is disposed between the inner layer 300 and the outer layer 200. The functional filter layer 100 includes a photoactive layer 110, the photoactive layer 110 includes a photocatalytic fiber having a core-shell structure, and the core-shell structure includes a core 400 having a polymer fiber and a shell having photocatalyst disposed at the core 400.

Figure 1B:
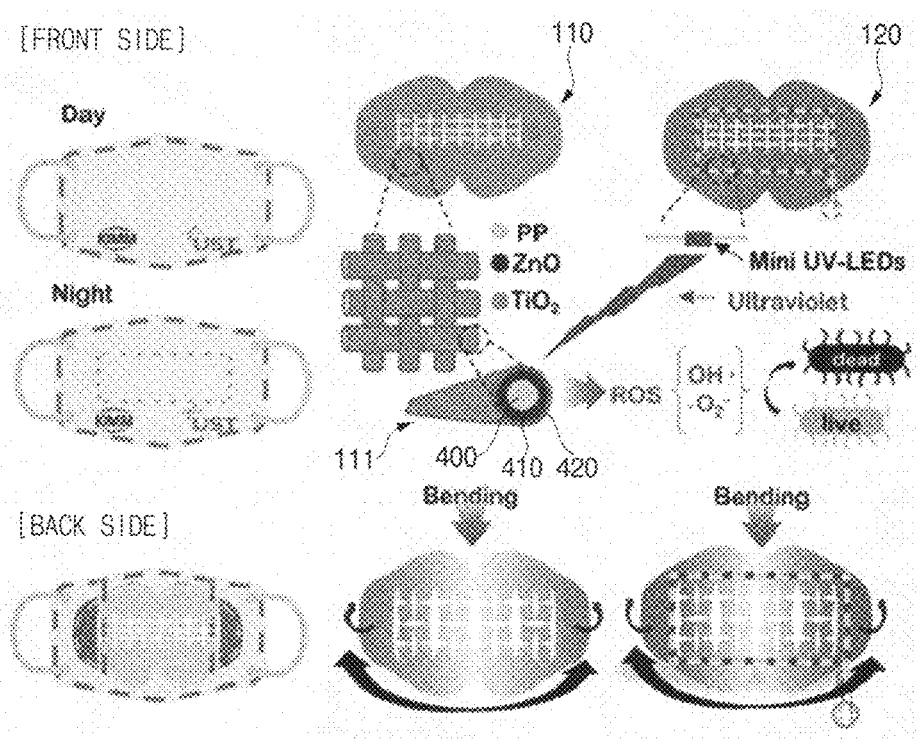
FIG. 1B is a conceptual view illustrating a photoactive layer and a light irradiation layer of the photocatalytic facial mask of FIG. 1A.

Referring to FIG. 1A, the facial mask 10 includes a mask body having the inner layer 300 and the outer layer 200, and the functional filter layer 100 disposed between the inner layer 300 and the outer layer 200. The inner and outer layers 300 and 200 have excellent breathability and have a material easily cleaned. For example, each of the inner and outer layers 300 and 200 may include a textile having at least one of fiber selected by a natural fiber such as cotton, linen, silk, and wool, an artificial fiber such as nylon, rayon, and modal, and a paper, but not limited thereto.

The functional filter layer 100 includes the photoactive layer 110 and a light irradiation layer 120 laminated with each other. The photoactive layer 110 includes the photocatalyst and has catalytic activity by light. The light irradiation layer 120 irradiates the light to the photocatalyst. Here, the photoactive layer 110 is disposed to face the outer layer 200, but not limited thereto, and thus the photoactive layer 110 may be disposed to face the inner layer 300.

Referring to FIG. 1B, the photoactive layer 110 includes the photocatalytic fiber 111 having a core-shell structure. For example, the shell of the photocatalytic fiber 111 may include a plurality of sheath layers in which at least two kinds of photocatalyst are laminated at the core 400. Here, when the plurality of sheath layers is included, selective charge distribution at an interface between the sheath layers of the photocatalyst may occur and recombination of electrons and electron holes may be restrained, and thus excellent photocatalytic activity may be realized.

The polymer fiber disposed at the core 400 of the photocatalytic fiber 111 may be one or at least two selected in the group including polyolefin, polyamide (nylon), polyester, acrylic polymer, polyurethane, rayon, and acetate polymer, but not limited thereto.

The diameter of the polymer fiber may be between about 0.1 $\mu$m and about 10 $\mu$m, and preferably between about 1 $\mu$m and 5 $\mu$m, but not limited thereto.

When the light is irradiated to the photocatalyst forming the shell of the photocatalytic fiber 111, the electrons and the electron holes are generated, to cause the generation of reactive oxygen species (ROS) such as hydroxyl radicals (OH), superoxide radicals ($O^{2-}$), and hydrogen peroxide ($H_2O_2$). The generated reactive oxygen species has a strong oxidizing effect and thus may inhibit cell growth and induce apoptosis, such as cell wall damage, mitochondrial weakening, intracellular outflow, and oxidative stress-induced gene expression.

The photocatalyst may include one or at least two selected in the group including titanium dioxide ($TiO_2$), zinc dioxide ($ZnO_2$), zinc oxide (ZnO), strontium titanate ($SrTiO_3$), cadmium sulfide (CdS), gallium phosphide (GaP), phosphorous phosphide (InP), gallium arsenide (GaAs), barium titanate ($BaTiO_3$), potassium niobate ($KNbO_3$), oxide iron (III) ($Fe_2O_3$), tantalum pentoxide ($Ta_2O_5$), tungsten trioxide ($WO_3$), tin oxide ($SnO_2$), triacid bismuth ($Bi_2O_3$), nickel oxide (NiO), copper oxide (I) ($Cu_2O$), silicon oxide (SiO), silicon dioxide ($SiO_2$), molybdenum disulfide ($MoS_2$), indium lead (InPb), ruthenium oxide (IV) ($RuO_2$), and cerium (IV) acid ($CeO_2$), but not limited thereto. Here, in at least two sheath layers having different photocatalysts, zinc oxide (ZnO) and titanium dioxide ($TiO_2$) may be preferably used.

For example, the photocatalytic fiber 111 may include a first sheath layer 410 and a second sheath layer 420. The first sheath layer 410 may have zinc oxide ZnO coated at the core 400 of the polymer fiber, and the second sheath layer 420 may have titanium dioxide $TiO_2$ formed on the first sheath. Here, zinc oxide ZnO and titanium dioxide $TiO_2$ are formed in series on the surface of the polymer fiber, to form the photocatalytic fiber 111 having the core-shell structure. Thus, the photocatalytic fiber 111 may be hydrophilic with a water contact angle less than about 90°, or preferably less than about 45°, or further preferably less than about 5°. Then, both oxygen and moisture in the air may become reactive oxygen species (ROS) such as hydroxyl radicals (OH), superoxide radicals ($O^{2-}$), and hydrogen peroxide ($H_2O_2$) due to the photocatalyst, and thus photocatalytic activity may be performed more effectively.

Since the photocatalytic fiber 111 is hydrophilic, as mentioned above, the moisture is effectively transformed to be reactive oxygen species (ROS) in a high humidity condition, so that bacteria or pathogen existing in the air flowing into the facial mask or exhausting from the facial mask may be destroyed effectively. In the conventional facial mask, the fiber having high hydrophobic material is used to block the bacteria or pathogen, but the hydrophobic characteristics of the fiber are decreased as time goes on and thus a blocking rate of the bacteria or pathogen is significantly decreased. However, in the present example embodiment, even though the use time of the facial mask increases, the blocking rate of the bacteria or pathogen is maintained due to the photocatalytic activity even in the high humidity condition.

A total thickness of the shell formed by the photocatalyst of the photocatalytic fiber may be between about 1 nm and about 100 nm, preferably between about 3 nm and about 80 nm, further preferably between about 5 nm and about 60 nm, and more further preferably between about 10 nm and about 50 nm.

A thickness of the first sheath layer 410 forming the shell may be between about 1 nm and about 60 nm, and preferably between about 10 nm and about 40 nm. A thickness of the second sheath layer 420 forming the shell may be between about 0.1 nm and about 30 nm, and preferably between about 1 nm and 15 nm. A ratio of the thickness between the first sheath layer 410 and the second sheath layer 420 may be between about 20:1 and about 1:5, preferably between about 10:1 and about 1:1, more preferably between about 8:1 and about 2:1, and thus the photocatalytic activity may be performed more effectively.

The light irradiation layer 120 irradiates the light to the photoactive layer 110. The light irradiation layer 120 always irradiates the light by user's operation, regardless of time or place.

A thickness of the photoactive layer 110 may be between about 100 nm and about 1,000 nm, and preferably between about 150 nm and about 700 nm, but not limited thereto.

The light irradiation layer 120 may include an electrode, a light source, and a battery formed on a surface of a textile. In addition, the light irradiation layer 120 may further include an operation part controlling an ON/OFF of the light source by the user.

A material of the textile may not be limited, but may be the same as the polymer fiber of the photoactive layer, or may be a polyimide.

The electrode formed on the surface of the textile may be formed via the conventional thin-film forming method, and for example, a conductive material is coated on the surface of the textile to form the electrode.

The light source may irradiate ultraviolet rays having a wavelength between about 200 nm and about 400 nm, and preferably between about 200 nm and about 230 nm. When the ultraviolet ray having the above wavelength is used, side effects caused by the light source irradiated from the facial mask worn on the face may be ignored, and the photoactive layer may be activated to perform excellent sterilization and antibacterial effect. The range of the wavelength of the light source may be properly changed according to the kinds of photocatalyst.

The functional filter layer 100 may be formed as a single unit having the photoactive layer 110 and the light irradiation layer 120 laminated with each other, so that the functional filter layer 100 may be easily inserted between the inner layer 300 and the outer layer 200, may be easily detached from the inner layer 300 and the outer layer 200, and may further be easily cleaned. The functional filter layer 100 is inserted into the body of the facial mask 10 and is disposed at the face of the user. In addition, the functional filter layer 100 has a kirigami pattern for the convenience of user's wear and use.

A method for forming the functional filter layer 100 as the single unit is not limited, and for example, the photoactive layer 110 and the light irradiation layer 120 is positioned to be overlapped with each other and then the photoactive layer 110 and the light irradiation layer 120 are combined with each other via stitching, heat bonding, adhesive, tape and so on.

The kirigami pattern may be the conventional kirigami pattern, and thus the functional filter layer 100 may be easily bent to fit the face of the user.

Hereinafter, a method for manufacturing the facial mask 100 mentioned above is explained in detail.

Figure 2:
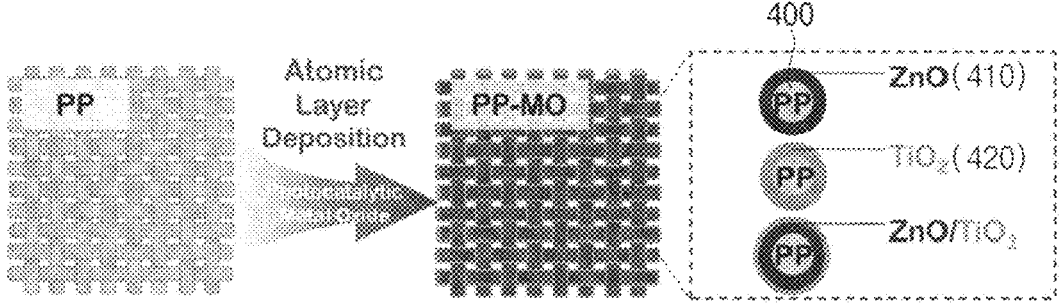
FIG. 2 is a process view illustrating a method for manufacturing the photoactive layer of the photocatalytic facial mask of FIG. 1A.
Figure 3A:
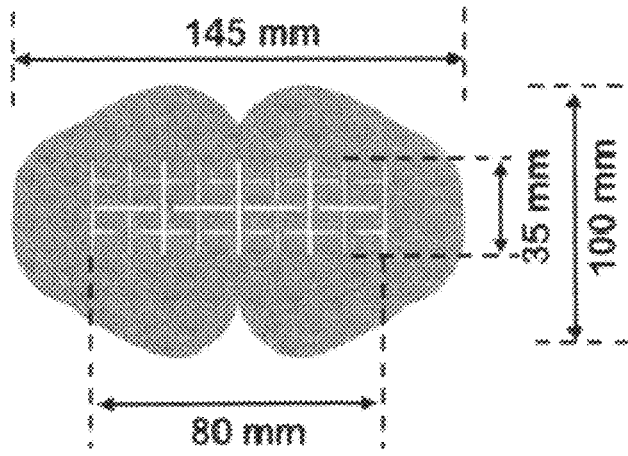
FIG. 3A is a front-side structural view illustrating a photocatalytic facial mask according to Example 1.
Figure 3B:
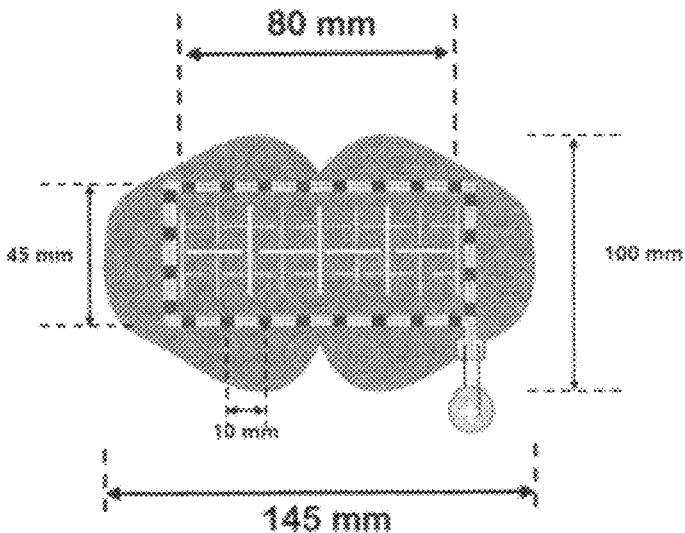
FIG. 3B is a back-side structural view illustrating the photocatalytic facial mask of FIG. 3A.
Figure 3C:
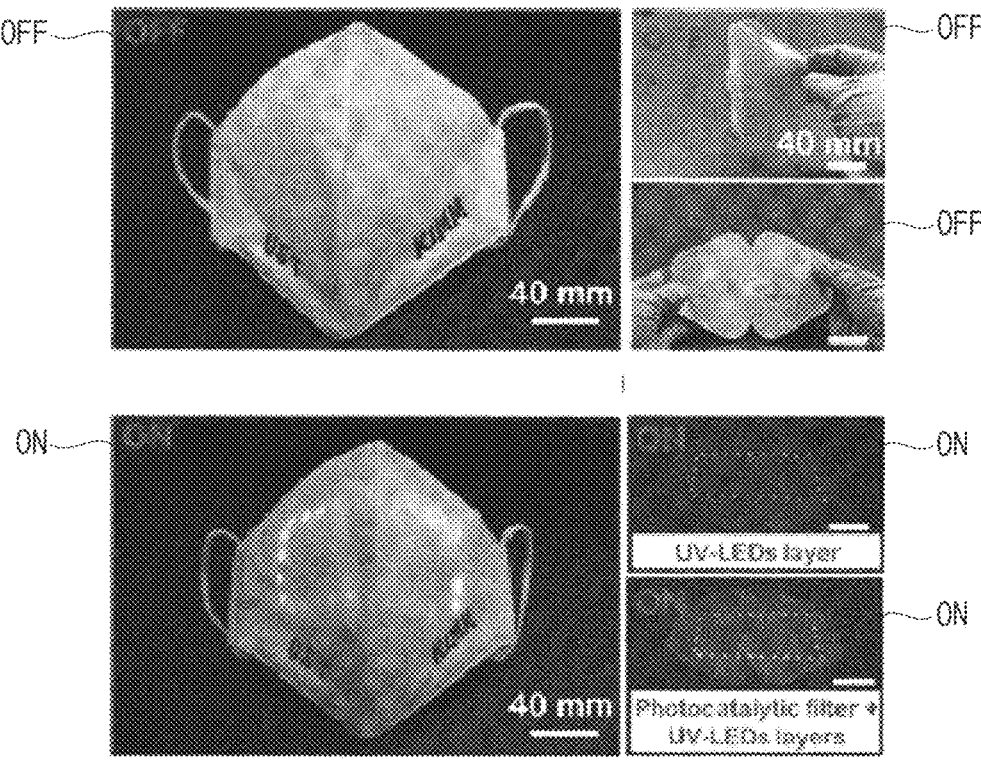
FIG. 3C is an image showing the photocatalytic facial mask of FIG. 3A.

FIG. 2 is a process view illustrating a method for manufacturing the photoactive layer of the photocatalytic facial mask of FIG. 1A. FIG. 3A is a front-side structural view illustrating a photocatalytic facial mask according to Example 1, FIG. 3B is a back-side structural view illustrating the photocatalytic facial mask of FIG. 3A, and FIG. 3C is an image showing the photocatalytic facial mask of FIG. 3A.

Referring to FIG. 2, FIG. 3A, FIG. 3B and FIG. 3C, in a method for manufacturing the facial mask 10, the photocatalyst is coated on the surface of the polymer fiber, to form the photoactive layer 110 including the photocatalytic fiber

111 having the core-shell structure. The electrode is formed on the surface of the textile and the light source is attached, to form the light irradiation layer 120. The photoactive layer 110 and the light irradiation layer 120 are combined with each other, to form the functional filter layer 100. The functional filter layer 100 is inserted between the inner layer 300 and the outer layer 400 of the facial mask 10.

In forming the photoactive layer 110, the above-mentioned same polymer fiber and the photocatalyst may be used. The photoactive layer 110 may be formed by the textile which is formed by weaving the photocatalyst fiber. Alternatively, as illustrated in FIG. 2, the photocatalyst may be coated on the textile which is formed by the above-mentioned same polymer fiber.

Here, the photocatalytic fiber 111 may include a plurality of sheath layers, and at least two kinds of photocatalyst may be coated and laminated at the core 400 of the polymer fiber to form the plurality of sheath layers. In coating the photocatalyst, the first photocatalyst is coated on the surface of the polymer fiber, and the second photocatalyst is coated on the first photocatalyst which is coated on the surface of the polymer fiber.

The photocatalyst may be coated via a deposition process such as an atomic layer deposition (ALD) or a chemical vapor deposition (CVD), a solution process in which photocatalytic precursor solution is coated on the core of the polymer fiber and then is transformed into the photocatalyst coating layer, and various kinds of conventional coating processes.

For example, via using the deposition like the ALD, the sheath layer may be uniformly formed at the core of the polymer fiber. Thus, a nano-sized shell may be effectively formed on the surface of the polymer fiber, and the photocatalytic fiber having the core-shell shape may be effectively formed.

The photocatalytic precursor forming the photocatalyst in the deposition or the solution process may be a compound satisfying Chemical formula 1.

$$M(A)_a(B)_b \qquad \text{[Chemical formula 1]}$$

In Chemical formula 1, M is a metal element. A and B are independent of each other and are $R^1$, $-OR^2$, $-N(R^3)(R^4)$, or a halogen element. $R^1$, $R^2$, $R^3$, $R^4$, $R^1$, and $R^6$ are independently substituted or unsubstituted C1(carbon number 1) to C6 linear or branched alkyl group, substituted or unsubstituted C6 to C15 aryl group, or substituted or unsubstituted C6 to C15 halogenated allyl group. a+b is an ionic value of M, and each of a and b is an integer with an ionic value or less. For example, the metal element M may be one or at least two selected in the group having Ti, Zn, Sr, Cd, Ga, In, Ba, Nb, Ta, W, Sn, Bi, Cu, Ga, Mo, Ru, and Ce.

A total thickness of the shell formed by the photocatalyst of the photocatalytic fiber 111 may be between about 1 nm and about 100 nm, preferably between about 3 nm and about 80 nm, further preferably between about 5 nm and about 60 nm, and more further preferably between about 10 nm and about 50 nm.

A thickness of the first sheath layer 410 forming the shell may be between about 1 nm and about 60 nm, and preferably between about 10 nm and about 40 nm. A thickness of the second sheath layer 420 forming the shell may be between about 0.1 nm and about 30 nm, and preferably between about 1 nm and 15 nm. A ratio of the thickness between the first sheath layer 410 and the second sheath layer 420 may be between about 20:1 and about 1:5, preferably between about 10:1 and about 1:1, more preferably between about 8:1 and about 2:1, and thus the photocatalytic activity may be performed more effectively.

A thickness of the photoactive layer 110 may be between about 100 nm and about 1,000 nm, and preferably between about 150 nm and about 700 nm, but not limited thereto.

The facial mask explained referring to FIG. 1A and FIG. 1B may be manufactured by the method mentioned above. The functional filter layer 100 may be formed as a single unit, so that the functional filter layer 100 may be easily inserted between the inner layer 300 and the outer layer 200, may be easily detached from the inner layer 300 and the outer layer 200, and the body of the facial mask 10 may be independently and easily cleaned for the multi-use. In addition, the functional filter layer 100 is disposed inside of the body of the facial mask 10, to be protected from the external impact or pollutant. In addition, the functional filter layer 100 includes the photoactive layer 110 having the photo-catalytic fiber 111 of the core-shell shape formed via the ALD process, and thus the photocatalyst may be prevented from being peeled and the safety may be enhanced, com-pared to the conventional photoactive layer which is formed by the material having the conventional binder and photo-catalyst.

Further, due to the light irradiation layer 120 of the functional filter layer 100, the photocatalyst of the photo-active layer 110 may be activated regardless of time and location. The photoactive layer 110 is hydrophilic, so that the photoactive layer 110 is reacted with both dissolved oxygen and moisture to form the reactive oxygen species (ROS). Thus, the photocatalytic activity in the facial mask 10 of the present exemplary embodiment may be enhanced, compared to the conventional facial mask.

Hereinafter, exemplary embodiments of the present invention and comparative examples are experimented to explain the facial mask 10 of the present invention in detail.

[Experimental Method]

1. Physical Property Evaluation

X-ray diffraction analysis was performed by Panalytical Empyrean diffractometer (Cu-Kα radiation, 40 kV, 30 mA, $\lambda=1.5418$ Å). UV-vis diffuse reflection spectrum (DRS) was measured by V-770 UV-VIS/NIR spectrophotometer.

2. Hydrophilicity Test

A water contact angle (CA) was measured by Drop Shape Analyzer system (DSA100, KRUSS GmbH).

3. Antibacterial Test

Figure 7:
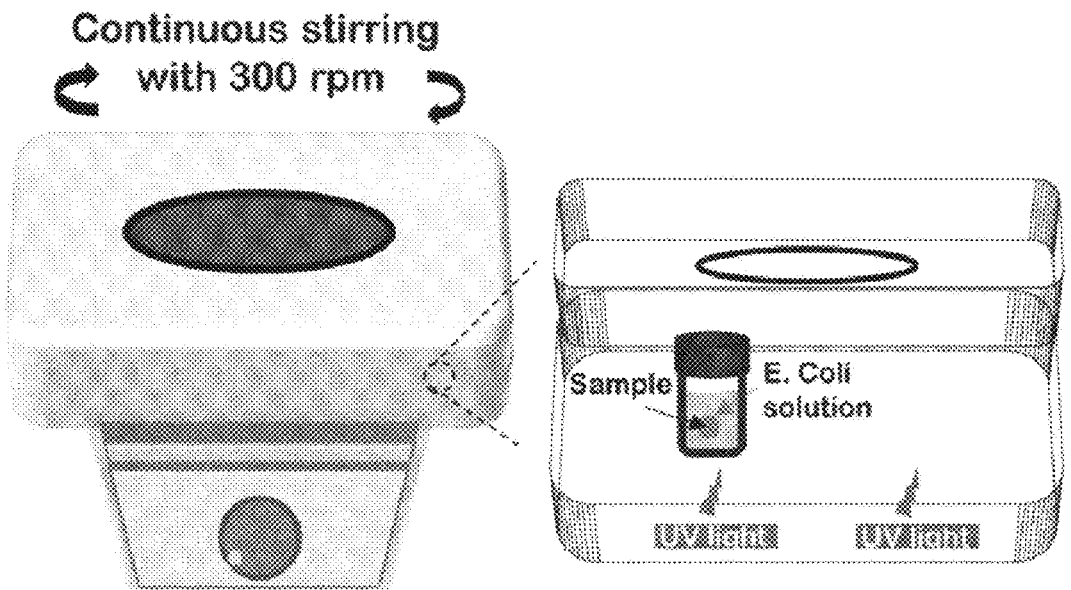
FIG. 7 is a schematic view illustrating an antibacterial test device used in the antibacterial test.

*E. coli* suspension 19 mL at a concentration of $5\times10^6$ CFUmL$^{-1}$ was pipetted into a glass vial, and a sample of the photoactive layer 110 cut with a circle having a diameter of 14 mm was inputted and then was enclosed. The antibacte-rial test device as illustrated in FIG. 7 which includes Standard Doctor Capsule Multi Sterilizer supporting ultra-violet ray UV-C ray and a shaker continuously shaking with 300 rpm, was used, and then the sample was reacted during each of 5, 10, 15, 20, 25 and 30 min. After the reaction, *E. coli* suspension 10 mL in the glass vial was pipetted into an agar plate and then cultivated. After incubation, antibacterial efficiency (or *E. coli* survival rate) was calculated via Formula 1.

$$E.\ coli\ \text{survival rate}=(C_0-C_t)/C_0 \qquad \text{[Formula 1]}$$

Here, $C_0$ is a number of colonies at an initial time of 0 min, and $C_t$ is a number of colonies at time of t min.

In addition, a recycling test was performed first after operating for 15 min. Then, the sample was cleaned with deionized water and then was dried at 70° C., and then the recycling test was performed second after operating 15 min with the same way of the first test.

Then, the test was performed five times in the same way as the first test.

Example 1

<Method for Forming the Photoactive Layer Via the ADL>

A polypropylene melt blown fabric having a thickness of 450 nm was cut with a rectangular shape of 5 cm length and 5 cm width, and then was inputted into the ALD chamber (S200, Savannah, Cambridge NanoTech Inc.). All deposi-tion processes were performed with an operating tempera-ture of 70° C. and a pressure of about 0.1 Torr.

For depositing ZnO, on the polypropylene melt blown fabric, diethyl zinc $Zn(C_2H_5)_2$ (DEZ) and deionized water were used as the precursor, and zinc oxide ZnO was depos-ited with the conditions of 0.02 sec pulse, 20 sec exposure, and 30 sec diethyl zinc (DEZ) purge, and then 0.1 sec pulse, 20 sec exposure and 30 sec deionized water purge. The above deposition was repeated, to form zinc oxide ZnO having the thickness of 25 nm on the polypropylene fiber as the first sheath layer.

Then, titanium dioxide $TiO_2$ was deposited as the second sheath layer, with the conditions of 1 sec pulse, 20 sec exposure, and 30 sec titanium isopropoxide purge, and then 1 sec pulse, 20 sec exposure, and 30 sec deionized water purge. The above deposition was repeated, to form the photoactive layer PP-Z25T5 which is formed with the photocatalytic fiber having the core-shell shape. Here, the photocatalytic fiber includes the first sheath layer, and the second sheath layer having titanium dioxide $TiO_2$ with the thickness of 5 nm coated on the first sheath layer.

<Method for Forming the Light Irradiation Layer>

As illustrated in FIG. 3A and FIG. 3B, a copper electrode having the thickness of 12 μm was formed on polyimide having the thickness of 50 μm, based on a flexible printed circuit board (FPCB), and then gold was electroplated for the passivation of the copper electrode, and then the elec-trode was formed.

As illustrated in FIG. 3A and FIG. 3B, UV-LED (LHUV-0385-A040, high power LED-single color UV 380 nm-390 nm, Lumileds, Mouser Electronics, Inc.) having a size of 1.7 mm*1.3 mm*0.68 mm was attached on the electrode, with the rectangular shape by a distance of 10 mm, via a solder paste based of tin. 3V coin battery (CR2030) was used as the battery and was inserted into a holder having an ON/OFF switch. Then, the light irradiation layer was formed.

<Method for Forming the Functional Filter Layer>

A fractal cut pattern (Proc. Natl. Acad. Sci. U.S.A. 2014, 111, 17390-17395) was formed on each of the photoactive layers and the light irradiation layer via a mass handle, and then two layers were combined to form the functional filter layer.

<Method for Forming the Photocatalytic Facial Mask>

The functional filter layer was inserted between the inner layer and the outer layer of the facial mask, and then the photocatalytic facial mask 10 was manufactured as illus-trated in FIG. 3C. As illustrated in FIG. 3C, by switching the ON/OFF switch of the facial mask, the UV-LED of the light irradiation layer may be controlled to be ON/OFF.

Example 2

The functional filter layer of Example 2 is the same as the functional filter layer of Example 1 except for not forming the titanium dioxide $TiO_2$ layer in the photoactive layer, and thus other processes are the same as explained above in Example 1. Thus, the photoactive layer PP-Z25 including the photocatalytic fiber in which the zinc oxide ZnO having the thickness of 25 nm is coated on the polypropylene fiber, is used for manufacturing the functional filter layer.

Example 3

The functional filter layer of Example 3 is the same as the functional filter layer of Example 1 except for not forming the zinc oxide ZnO layer in the photoactive layer, and thus other processes are the same as explained above in Example 1. Thus, the photoactive layer PP-T25 including the photocatalytic fiber in which titanium dioxide $TiO_2$ having the thickness of 25 nm is coated on the polypropylene fiber, is used for manufacturing the functional filter layer.

Example 4

The functional filter layer of Example 4 is the same as the functional filter layer of Example 1 except for forming titanium dioxide $TiO_2$ having the thickness of 15 nm in the photoactive layer, and thus other processes are the same as explained above in Example 1. Thus, the photoactive layer PP-Z25T15 is used for manufacturing the functional filter layer.

Example 5

The functional filter layer of Example 5 is the same as the functional filter layer of Example 1 except for forming titanium dioxide $TiO_2$ having the thickness of 25 nm in the photoactive layer, and thus other processes are the same as explained above in Example 1. Thus, the photoactive layer PP-Z25T25 is used for manufacturing the functional filter layer.

Characteristic evaluation on the above Comparative example embodiment and Examples are as follows.

[Experimental Example 1] Composition and Structure of the Photoactive Layer

Figure 4A:
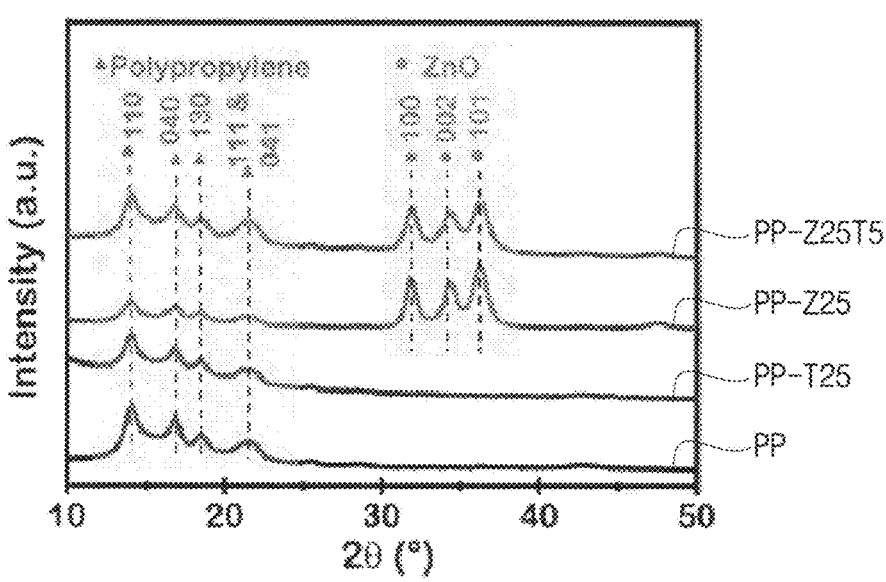
FIG. 4A and FIG. 4B are graphs showing the composition of photocatalytic facial masks according to Example 1, Example 2 and Example 3.
Figure 4B:
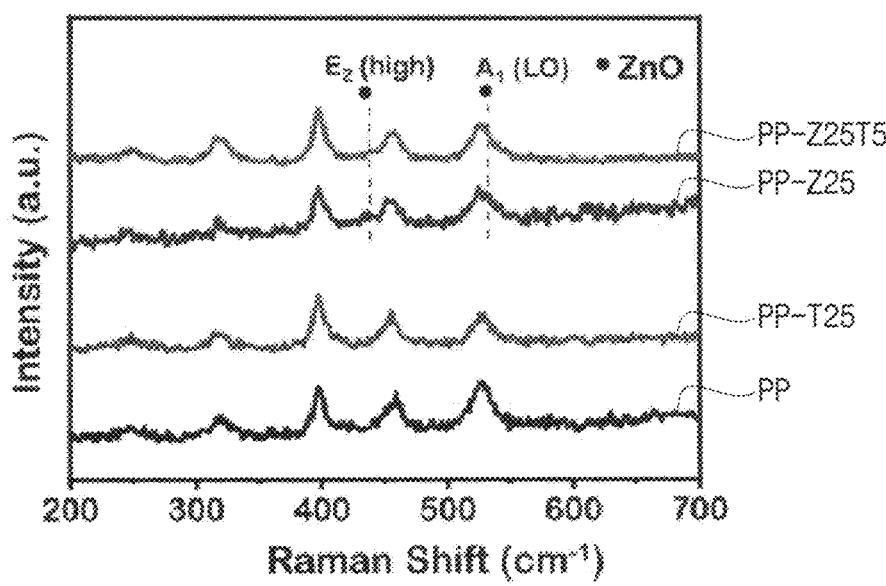
Figure 4C:
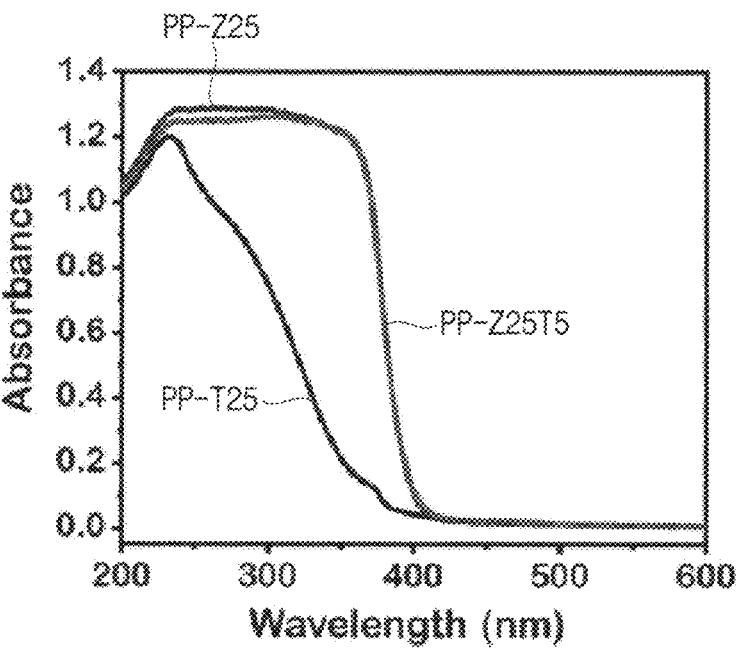
FIG. 4C and FIG. 4D are graphs showing characteristics of the photocatalytic facial masks according to Example 1, Example 2, and Example 3.
Figure 4D:
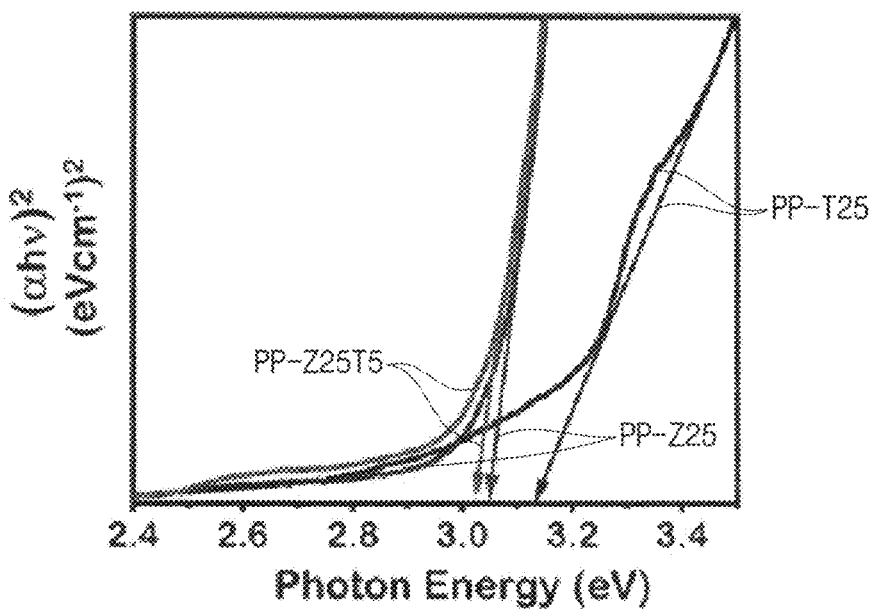
Figure 5A:
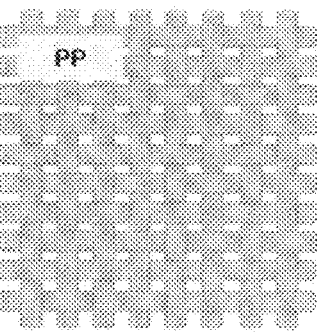
FIG. 5A, FIG. 5B, FIG. 5C and FIG. 5D are images showing evaluation results for hydrophilicity characteristics of the photoactive layer of the photocatalytic facial masks according to Example 1, Example 2, and Example 3.
Figure 5A:
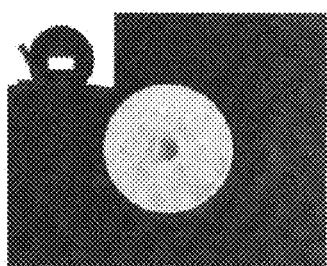
Figure 5B:
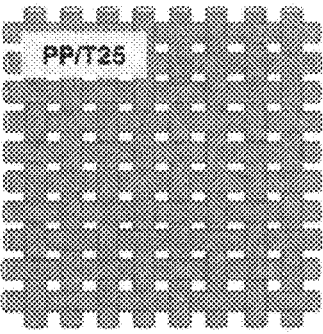
Figure 5B:
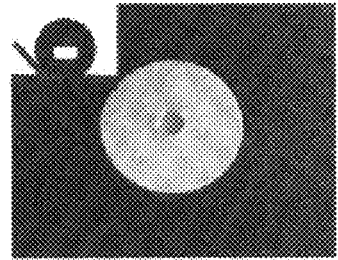
Figure 5C:
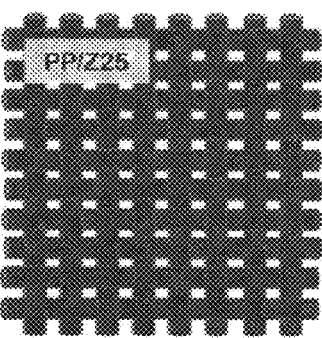
Figure 5C:
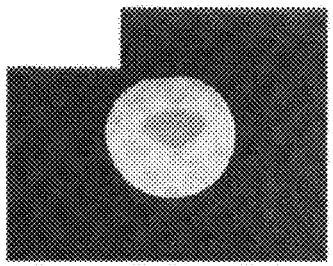
Figure 5D:
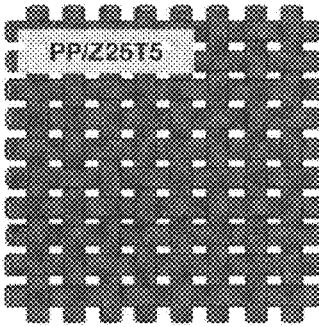
Figure 5D:
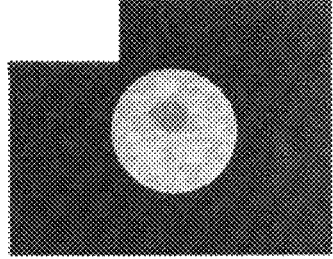

FIG. 4A and FIG. 4B are graphs showing the composition of photocatalytic facial masks according to Example 1, Example 2 and Example 3, and FIG. 4C and FIG. 4D are graphs showing characteristics of the photocatalytic facial masks according to Example 1, Example 2, and Example 3.

Specifically, FIG. 4A shows the XRD pattern of the photoactive layer manufactured in Example 1, Example 2, and Example 3, FIG. 4B shows the Raman spectrum of the photoactive layer manufactured in Example 1, Example 2, and Example 3, FIG. 4C shows the UV-visible diffusion reflection spectrum of the photoactive layer manufactured in Example 1, Example 2, and Example 3, and FIG. 4D shows $((\alpha h v)^2$ plot according to a photon energy of the photoactive layer manufactured in Example 1, Example 2, and Example 3.

Referring to FIG. 4A, five diffraction peaks at 14.0°, 16.7°, 18.4°, 21.0°, and 21.8° respectively correspond to grid planes of (110), (040), (130), (111) and (041) of polypropylene. 30 XRD patterns in Example 2 (PP-Z25) and Example 1 (PP-Z25T5) show traditional diffraction peaks related to ZnO, at 31.7° (100), 34.4° (002), and 36.4° (101). However, the diffraction peak of $TiO_2$ is not observed in Example 3 (PP-T25) and Example 1 (PP-Z25T5). This means that the anatase phase may not be formed except for amorphous when the deposition temperature of $TiO_2$ is 70° C.

Referring to FIG. 4B, Raman spectrum of polypropylene melt blown fabric (PP) and the photoactive layer in Examples 1 to 3 is shown. The value in Example 2 (PP-Z25) and Example 1 (PP-Z25T5) is 438.25 cm$^{-1}$ at E2 (high) and is 533.16 cm$^{-1}$ at A1 (L0). In addition, the peak value of E2 (high) mode observed near between 430.0 cm$^{-1}$ and 460.0 cm$^{-1}$ shows the characteristics of the ZnO wurtzite structure. Thus, in XRD and Raman characteristics, ZnO having a nano-size deposited on PP has a wurtzite hexagon shape and is the same as ZnO of ZnO—$TiO_2$ of Example 1.

FIG. 4C shows the UV-visible diffusion reflection spectrum of the photoactive layer manufactured in Example 1, Example 2, and Example 3, and FIG. 4D shows $(\alpha h v)^2$ plot according to photon energy (hv) of the photoactive layer manufactured in Example 1, Example 2, and Example 3.

A direct bandgap (Eg) of the photoactive layers (PP-Z25T5, PP-Z25, and PP-T25) in Examples 1 to 3 was obtained by extrapolating the straight line of $(\alpha h v)^2$ plot according to photon energy (hv) at $\alpha$=0, based on Equation 1 of Tauc below.

$$(\alpha h v)^2 = A(h v - Eg) \qquad \text{[Equation 1]}$$

$$h v = 1240/\lambda \qquad \text{[Equation 2]}$$

Here, $\alpha$ is a light absorption coefficient calculated at absorbance A, hv (eV) is an estimated value using Equation 2.

The absorption spectrum between 200 nm and 500 nm in Example 1(PP-Z25T5) and Example 2 (PP-Z25) was stronger than that in Example 3 (PP-T25), in the UV visible region, and the redshift of the bandgap transition was suitable for electron transport. The bandgaps of PP-Z25T5, PP-Z25 and PP-T25 were respectively estimated to 3.02 eV, 3.05 eV and 3.12 eV. The energy decrease of the bandgap of ZnO—$TiO_2$ of Example 1 (PP-Z25T5) may be caused by a synergy effect between conduction bands of ZnO and $TiO_2$.

[Experimental Example 2] Hydrophilicity Characteristic Evaluation of the Photoactive Layer FIG. 5A, FIG. 5B, FIG. 5C and FIG. 5D are images showing evaluation results for hydrophilicity characteristics of the photoactive layer of the photocatalytic facial masks according to Example 1, Example 2, and Example 3.

As illustrated in FIG. 5A, FIG. 5B, FIG. 5C and FIG. 5D, the photoactive layer in Example 1 (PP-Z25T5) has excellent hydrophilicity with the contact angle of 0°, compared to the photoactive layers in Example 2 (PP-Z25) and Example 3 (PP-T25). This means that more improved antibacterial properties may be realized since the photocatalyst generates the reactive oxygen species (ROS) not only in dissolved oxygen molecules but also in water.

[Experimental Example 3] Antibacterial Property Evaluation of the Functional Filter FIG. 6A, FIG. 6B, FIG. 6C and FIG. 6D are graphs showing antibacterial test results in the UV environment for the photoactive layer of the photocatalytic facial masks according to Example 1, Example 2, and Example 3.

Figure 6A:
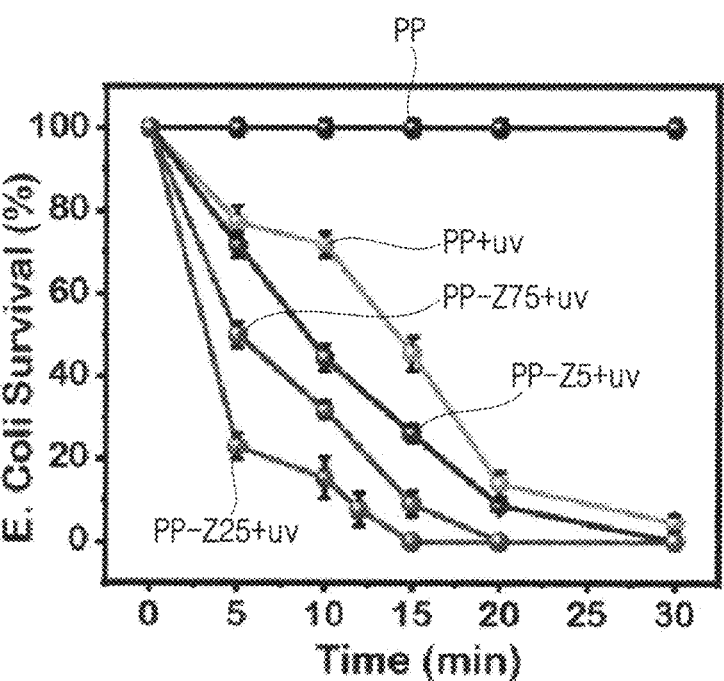
FIG. 6A, FIG. 6B, FIG. 6C and FIG. 6D are graphs showing antibacterial test results in the UV environment for the photoactive layer of the photocatalytic facial masks according to Example 1, Example 2, and Example 3.
Figure 6B:
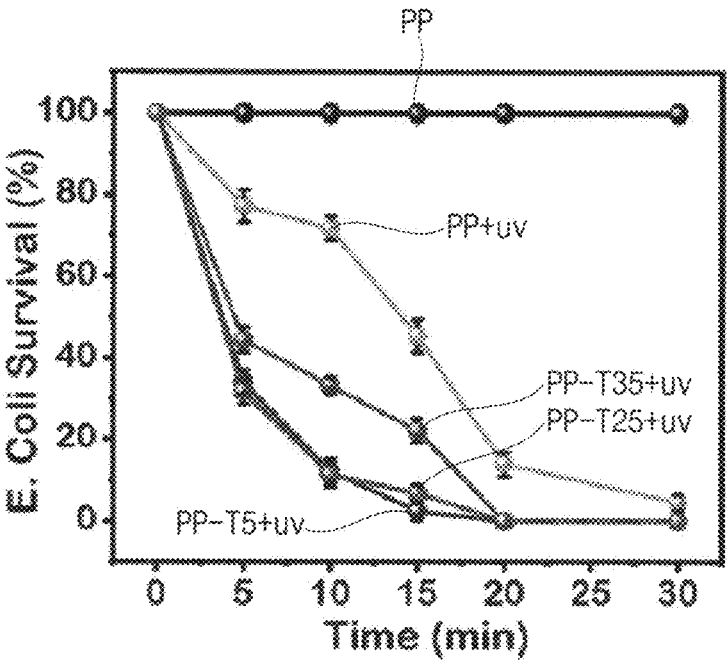
Figure 6C:
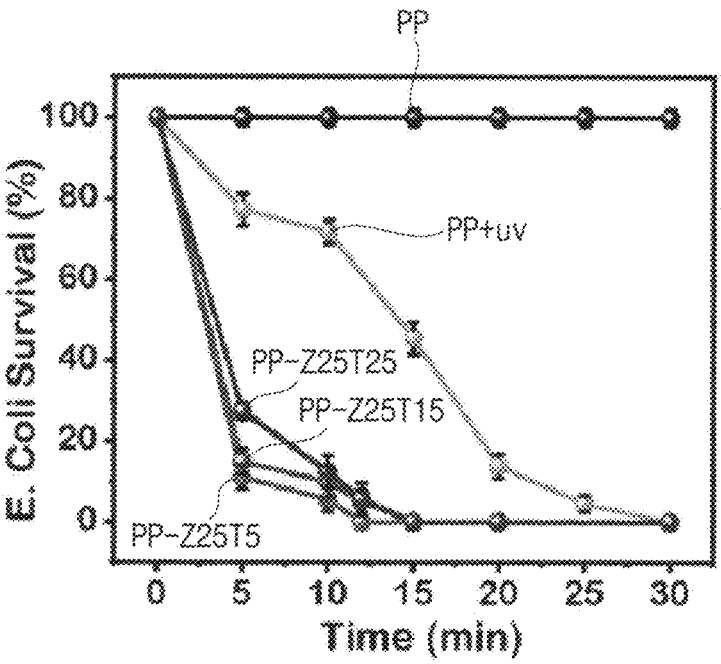

Specifically, FIG. 6A shows the antibacterial property of the photoactive layer in Example 2 (PP-Z25), FIG. 6B shows the antibacterial property of the photoactive layer in Example 3 (PP-T5), FIG. 6C shows a survival curve of *E.*

Figure 6D:
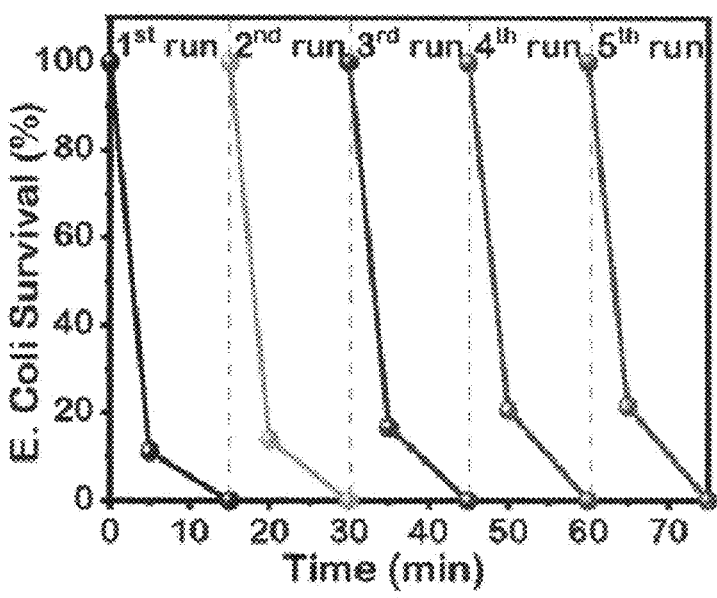

*coli* of the photoactive layers in Example 1, Example 4 and Example 5, and FIG. 6D shows the antibacterial recycling property of the photoactive layer in Example 1.

As illustrated in FIG. 6C, the photoactive layers in Example 1, Example 4 and Example 5 have excellent initial antibacterial properties compared to the layer (PP+uv) which is formed by merely irradiating the ultraviolet ray to the polypropylene melt brown fabric PP, and have excellent initial *E. coli* apoptosis compared to the photoactive layers in Example 2 and Example 3. These results coincide with the result of the photoactive layer having the contact angle of 0° in the above hydrophilicity characteristic evaluation. In addition, the initial antibacterial property of the photoactive layer in Example 1 (PP-Z25T5) in which the thickness of titanium dioxide $TiO_2$ of the shell of the photocatalytic fiber is 5 nm, is better than that of each of the photoactive layers in Example 4 (PP-Z25T15) and Example 5 (PP-Z25T25) in which the thickness of titanium dioxide $TiO_2$ of the shell of the photocatalytic fiber are 15 nm and 25 nm respectively.

In addition, as illustrated in FIG. 6D, after the photoactive layer is cleaned and dried more than two times, the antibacterial property of the photoactive layer is not changed and is maintained, compared to the initial antibacterial property thereof.

According to the present example embodiments, in the facial mask, the photoactive layer having a core-shell structure photocatalytic fiber is disposed between the inner layer and outer layer, and thus the photocatalytic activity may be generated in the irradiation of the light, and excellent antibacterial properties may be performed. In addition, the functional filter layer having a laminated structure of the light irradiation layer is used, so that the photocatalytic activity may operate all the time regardless of the irradiation of the light, the time, and the location. Here, the light irradiation layer has the light source irradiating the light to the photoactive layer.

In addition, the functional filter layer is disposed between the inner layer and the outer layer of the mask, and thus the functional filter layer is protected from the contamination or the damage from outside, and the user easily inserts the functional filter layer between the inner layer and the outer layer or detaches the functional filter layer.

Further, the photoactive layer included in the photocatalytic facial mask has the core-shell structure in which the core 400 has a polymer fiber and the shell having the photocatalyst disposed at the core 400. Thus, selective charge separation at the core-shell interface and suppression of the recombination of the electrons and the electron holes are performed so that the photocatalytic activity may be efficiently obtained.

Although the exemplary embodiments of the present invention have been described, it is understood that the present invention should not be limited to these exemplary embodiments but various changes and modifications can be made by one ordinary skilled in the art within the spirit and scope of the present invention as hereinafter claimed.

What is claimed is:

1. A facial mask comprising:
an inner layer;
an outer layer; and
a functional filter layer disposed between the inner layer and the outer layer,
wherein
the functional filter layer includes a photoactive layer, the photoactive layer includes a photocatalytic fiber having a core-shell structure, the core-shell structure includes a core having a polymer fiber and a shell having photocatalyst disposed on the core, the shell includes a first sheath layer having zinc oxide directly on the core and a second sheath layer having titanium dioxide on the first sheath layer, the first sheath layer has a thickness of 1 nm to 60 nm and the second sheath layer has a thickness of 0.1 nm to 30 nm, and the zinc oxide has a wurtzite structure and the titanium dioxide has an amorphous structure.

2. The facial mask of claim 1, wherein the functional filter layer further comprises:

a light irradiation layer having a light source configured to irradiate light to the photoactive layer, wherein the light irradiation layer and the photoactive layer are laminated with each other.

3. The facial mask of claim 2, wherein the light irradiation layer comprises an electrode, the light source and a battery disposed on a surface of a textile.

4. The facial mask of claim 2, wherein the light source irradiates ultraviolet rays having a wavelength between 200 nm and 400 nm.

5. The facial mask of claim 1, wherein the shell of the photocatalytic fiber has a thickness between 1 nm and 100 nm.

6. The facial mask of claim 1, wherein a ratio of the thickness between the first sheath layer and the second sheath layer is between 8:1 and 2:2.

7. The facial mask of claim 1, wherein a water contact angle of the photoactive layer is less than 45°.

8. The facial mask of claim 1, wherein the functional filter layer has a fractal cut pattern.

9. The facial mask of claim 1, wherein the first sheath layer has a thickness of 10 nm to 40 nm.

10. The facial mask of claim 1, wherein the second sheath layer has a thickness of 1 nm to 15 nm.

11. A method for manufacturing a facial mask comprising:

coating photocatalyst on a surface of a polymer fiber, to form a photoactive layer including a photocatalytic fiber having a core-shell structure;

forming an electrode on a surface of a textile and attaching a light source, to form a light irradiation layer;

combining the photoactive layer and the light irradiation layer with each other, to form a functional filter layer; and inserting the functional filter layer between an inner layer and an outer layer of the facial mask, wherein the core-shell structure includes a core and a shell, the shell includes a first sheath layer having zinc oxide directly on the core and a second sheath layer having titanium dioxide on the first sheath layer, the first sheath layer has a thickness of 1 nm to 60 nm and the second sheath layer has a thickness of 0.1 nm to 30 nm, and the zinc oxide has a wurtzite structure and the titanium dioxide has an amorphous structure.

12. The method of claim 11, wherein the photocatalyst is coated via an atomic layer deposition (ALD) or a chemical vapor deposition (CVD).

13. The method of claim 11, wherein the photocatalytic fiber is formed by:

coating a first photocatalyst on the surface of the polymer fiber; and coating a second photocatalyst on the first photocatalyst.

14. A facial mask manufactured by the method of claim 11.

\* \* \* \* \*